United States Patent [19]

Makiej, Jr.

[11] Patent Number: 5,002,048

[45] Date of Patent: Mar. 26, 1991

[54] INHALATION DEVICE UTILIZING TWO OR MORE AEROSOL CONTAINERS

[76] Inventor: Walter J. Makiej, Jr., 70 Mount Hope St., Lowell, Mass. 01859

[21] Appl. No.: 449,575

[22] Filed: Dec. 12, 1989

[51] Int. Cl.⁵ .................... A61M 11/00; A61M 15/00; B67D 5/52; B67D 5/60

[52] U.S. Cl. .......................... 128/200.23; 128/203.12; 222/135; 222/145

[58] Field of Search ....................... 128/200.23, 203.12, 128/200.14, 200.19, 203.14, 205.21; 222/135, 145, 402.15

[56] References Cited

U.S. PATENT DOCUMENTS

| | | | |
|---|---|---|---|
| 3,451,593 | 6/1969 | Dillarstone | 222/135 |
| 3,704,725 | 12/1972 | Marand | 222/145 |
| 3,908,868 | 9/1975 | Peirish, Jr. | 222/145 |
| 3,916,343 | 12/1975 | Kleiner | 222/145 |
| 3,923,202 | 12/1975 | Riccio | 222/145 |
| 4,261,481 | 4/1981 | Speer | 222/135 |
| 4,593,836 | 6/1986 | Lilienthal | 222/135 |
| 4,791,149 | 12/1988 | Pocknell | 222/135 |
| 4,887,591 | 12/1989 | Okumura | 128/205.21 |
| 4,953,547 | 9/1990 | Poole, Jr. | 128/203.12 |

Primary Examiner—Edgar S. Burr
Assistant Examiner—Kimberly L. Asher
Attorney, Agent, or Firm—Wolf, Greenfield & Sacks

[57] ABSTRACT

The invention includes an inhalation device for delivering medication from two or more medicinal aerosol containers. An L-shaped housing includes a mouthpiece opening at one end and chambers at the other end for receiving the medicinal aerosol containers.

10 Claims, 1 Drawing Sheet

INHALATION DEVICE UTILIZING TWO OR MORE AEROSOL CONTAINERS

FIELD OF THE INVENTION

The present invention relates to inhalation devices and, more particularly, relates to inhalation devices for delivering multiple medications.

BACKGROUND OF THE INVENTION

Therapeutic efficiency is often improved by treating patients with a combination of medications. Asthma treatment is representative of such methods; as a rule, a beta-adrenergic product or a cromolyn sodium product is first delivered to dilate the bronchial passageways after which a corticosteroid is administered to reduce inflammation.

Typically, these medications are delivered as inhalational medications. Under conventional practice, a patient uses one metered dose inhaler to deliver the bronchodilator and another metered dose inhaler to deliver the corticosteroid. The practice of using multiple inhalers is inconvenient and burdensome. Often times a patient will misplace one of the inhalers and then simply administer the drug contained in the remaining inhaler with the obvious detriment to therapeutic efficacy resulting. Patients already self-conscious of the fact that they are publicly taking medication are likely to skip scheduled administrations during working or school hours when multiple inhalers have to be utilized. Accordingly, the prior art lacks a single device capable of delivering inhalation medications administered in combination.

SUMMARY OF THE INVENTION

The present invention includes an inhalation device for administering medications from different aerosol containers supported thereon. Two aerosol containers are supported relative to a mouthpiece opening. Respective valve assemblies are provided to direct the metered dose spray towards the mouthpiece upon actuation by the patient. The valve assemblies are positioned so that the aerosolized spray upon discharge passes unimpeded towards the mouthpiece opening. A dividing wall may be provided to separate the fluid paths of different medicinal sprays. In one embodiment, the two aerosol containers are aligned perpendicular to the longitudinal axis of the mouthpiece. In another embodiment, the two aerosol containers extend radially relative to the mouthpiece.

It is a primary object of the present invention to provide an inhalation device for administering medication from multiple aerosol containers.

It is a further object of the present invention to provide an inhalation device that is simple and inexpensive to manufacture.

It is still another object of the present invention to provide an inhalation device that facilitates administration of complementary medications.

BRIEF DESCRIPTION OF THE DRAWING

These and other details and advantages of the invention will be described in connection with the accompanying Drawing in which.

DESCRIPTION OF THE PREFERRED EMBODIMENT

Figure 1:
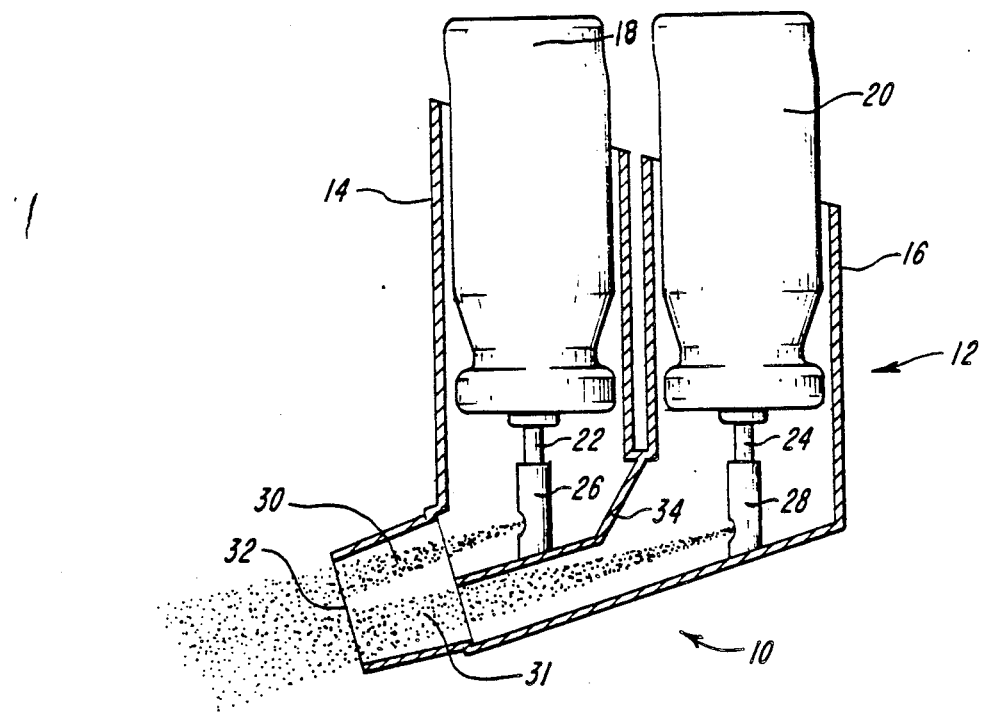
FIG. 1 is a perspective view partly in phantom of the inhalation device according to a preferred embodiment of the invention.

In the preferred embodiment of the present invention as shown in FIG. 1, the inhalation device 10 includes an L-shaped housing 12 having first and second chambers 14, 16 which may be aligned with one another. Aerosol canisters or containers 18, 20 containing the medicine to be administered are received within the chambers 14, 16. Exit tubes 22, 24 are positioned in the opening of the valve discharge assemblies 26, 28. As is well known to those skilled in the art, displacement of the aerosol container against the valve discharge assemblies will cause the pressurized medication stored in the container to escape through the exit tubes and into the valve assemblies. The valve assemblies discharge the aerosolized medication 30, 31 towards and through the mouthpiece opening 32. Valve assembly 28 is disposed below valve assembly 26 to provide an unobstructed fluid path for the aerosolized medicinal spray to follow towards the mouthpiece opening 32. Chamber 16 is preferably positioned so that container 20 extends to a lesser height than container 18. The distinction in height between the two containers 18, 20 is thought to facilitate the patients recognition of the different medications being actuated. Also having the Beta$_2$ product appearing in front of the corticosteroid product is believed to further facilitate the patient's recognition as to which medication to take first.

To prevent the aerosolized sprays from mixing prior to administration and to prevent medicinal remnants on the housing inner surface from contaminating subsequent actuations, a dividing wall 34 is preferably disposed between the first and second valve assemblies. The dividing wall 34 extends across the housing 12 from one side to the other and lengthwise at least a sufficient amount to ensure that the aforementioned disadvantages are minimized. The greatest guarantee against deleterious mixing and contamination is achieved by having the dividing wall 34 extend all the way to the mouthpiece opening 32.

Figure 2:
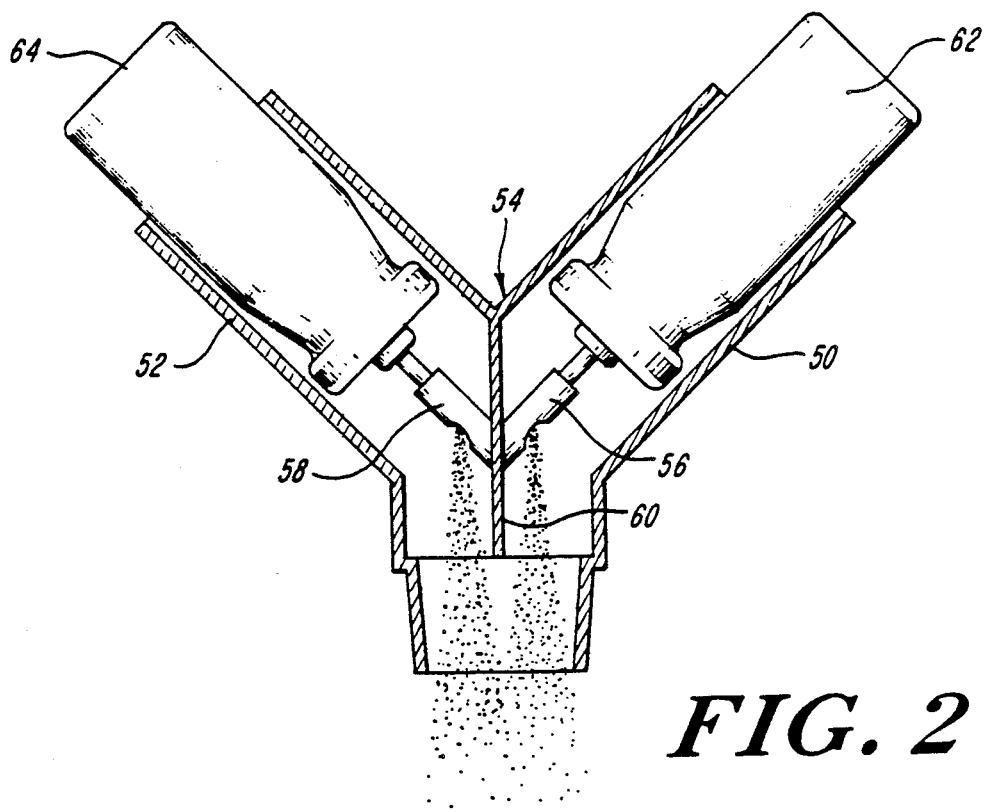
FIG. 2 is a top view partly in phantom showing an alternative embodiment of the invention.

In an alternative embodiment shown in FIG. 2 the chambers 50, 52 for receiving the containers holding the pressurized medicine extend radially from the housing 54. To facilitate manufacture of the inhalation device, the valve assemblies 56, 58 are aligned with the chambers 50, 52. Dividing wall 60 is disposed between the valve assemblies 56, 58 to prevent disadvantageous contamination or commingling of the different medications discharged from the first and second containers 62, 64.

Application of complementary medications is facilitated by use of the present invention. A representative example is the treatment of asthma. In the dual chamber inhalation device according to the present invention, one of the aerosol containers holds a bronchodilator such as albuterol while the other aerosol container holds the corticosteroid such as beclomethasone dipropionate. The patient places the mouthpiece into his/her mouth and then depresses the aerosol container holding the albuterol whereby a metered dose of albuterol is discharged from the aerosol container through the exit tube and out of the valve towards and through the mouthpiece opening and into the patients bronchial passageways. After a predetermined period of time in which the albuterol operates to open the bronchial channels, the patient depresses the other aerosol container whereby the beclomethasone dipropionate is administered to the patient via the same route through the inhalation device. The anti-inflammatory corticosteroid can travel deep into the patients bronchial tract by virtue of the prior bronchodilation therapy. Accordingly, increased therapeutic efficiency of the inhaled beclomethasone dipropionate is achieved. Also by using the corticosteroid after the bronchodilator the patient will reduce inflammation and enhance the effectiveness of the subsequent bronchodilator administration. Consequently, using a Beta$_2$ and an inhaled corticosteroid combination drug regimen optimizes the total therapeutic efficiency of both drugs.

It is to be understood that the preceding description is given merely by way of illustration and not in limitation of the invention and that various modifications may be made thereto without departing from the spirit of the invention as claimed.

What is claimed is:

1. An inhalation device, comprising:
   a housing with a first end having at least two openings, each of said at least two openings adapted to receive an aerosol container containing a medicinal compound;
   said housing having a second end with an opening in communication with the outside;
   said housing further having a hollow chamber in communication with said opening at said second end and means contiguous with said hollow chamber for discharging the medicinal compound from the aerosol containers through said hollow chamber and out of the opening in the second end in communication with the outside.

2. The inhalation device recited in claim 1 wherein said means for discharging includes individual means for discharging the medicinal compound from each of the aerosol containers.

3. The inhalation device recited in claim 2 further comprising means for dividing said hollow chamber into a plurality of hollow chambers corresponding to the number of said individual discharging means, each of said plurality of hollow chambers being in communication with one of said individual discharging means and said opening at said second end.

4. The inhalation device recited in claim 3 wherein said means for dividing includes a dividing wall extending from a first interior side of said housing to a second interior side of said housing between adjacent of said individual discharging means.

5. The inhalation device recited in claim 4 wherein said dividing wall extends between said individual discharging means and said opening at said second end.

6. An inhalation device, comprising:
   a housing having a first end and a second end disposed in an L-shaped relationship, said first end having first and second aligned cavities adapted to receive first and second aerosol containers each of which contain a medicinal component, said first cavity being disposed between said second end and said second cavity;
   said second end having an opening in communication with the outside;
   said housing further having a hollow chamber in communication with said opening at said second end; and
   first means contiguous with said hollow chamber for discharging the medicinal component from the first aerosol container in a first fluid path towards and through said hollow chamber and out of said opening in said second end and second means contiguous with said hollow chamber for discharging the medicinal component in a second fluid path from the second aerosol container towards and through said hollow chamber and out of said opening in said second end.

7. The inhalation device recited in claim 6 wherein said housing further includes means for supporting said first and second means for discharging so that the second fluid path does not intersect said first means for discharging.

8. The inhalation device recited in claim 6 further including means for dividing said hollow chamber into a first chamber that permits communication between said first means for discharging and said opening at said second end and a second chamber that permits communication between said second means for discharging and said opening at said second end.

9. The inhalation device recited in claim 8 wherein said dividing means includes a dividing wall extending from a first interior side of said housing to a second interior side of said housing between said first and second means for discharging.

10. An inhalation device comprising:
    a housing having a first end and a second end, said first end having first and second spaced radial extensions thereof, each of said first and second spaced radial extensions having an opening adapted to receive an aerosol container containing a medicinal component;
    said second end having an opening in communication with the outside;
    said housing further having a hollow chamber in communication with said opening at said second end; and
    first means contiguous with said hollow chamber for discharging the medicinal component from the first aerosol container in a first fluid path towards and through said hollow chamber and out of said opening in said second end and second means contiguous with said hollow chamber for discharging the medicinal component in a second fluid path from the second aerosol container towards and through said hollow chamber and out of said opening in said second end.

* * * * *